Sept. 10, 1963 P. P. ZAMPINI Plant Pat. 2,284
CLIMBING WHITE ROSE PLANT
Filed June 5, 1961
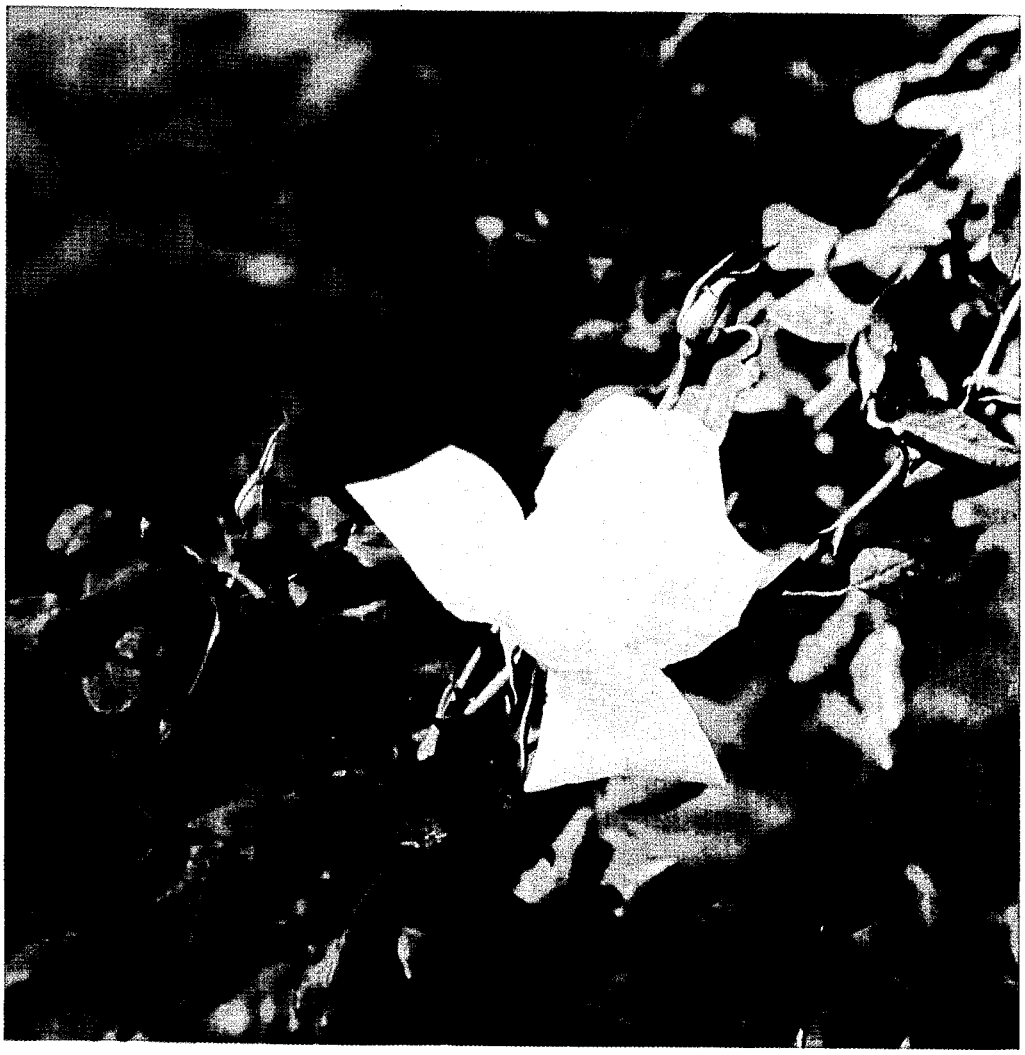
INVENTOR
PHILIP P. ZAMPINI
BY Bosworth, Sessions, Herrstrom & Knowles
ATTORNEYS United States Patent Office Plant Pat. 2,284
Patented Sept. 10, 1963

2,284

CLIMBING WHITE ROSE PLANT

Philip P. Zampini, 636 W. Main St., Geneva, Ohio

Filed June 5, 1961, Ser. No. 115,055
1 Claim. (Cl. Plt.—3)

This invention relates to a new and distinct variety of climbing rose plant of the hybrid tea class which originated by breeding and development of a sport of Edith Krause, not patented.

It is distinguished by its white blooms; by the full form and fragrance of its blooms; by its vigorous growth; and, by its heavy canes.

Asexual reproduction of this new white climbing rose plant variety by budding in gardens located in Perry, Ohio, shows that the characteristics and distinctions set forth herein come true to form and are established and transmitted through succeeding generations.

The accompanying drawing shows a typical flower specimen of the new variety of climbing rose plant together with some of the stems and leaves.

In the following detailed description color plate numbers refer to Maerz and Paul's "A Dictionary of Color," first edition.

*The Plant*

Growth: Vigorous—average height about four feet first year.
Form: Climber.
Blooming habit: Everblooming.
Canes: Heavy, 7/16" to ½" in diameter.
Height: Maximum cane height, first year, about five feet.
Thorns: Medium, red, 3K9, outward pointing and sharp, about ¼ inch long.
Stems: Six inches long, green, 20L7, reddish cast in color.
Leaves: Smallish, elongated, outwardly pointed, leaflets of 5 to 7, medium green, 23E11, about 1½ inches long by ⅞ inch wide.

Pods: Round, green 20L5, having 8 to 14 irregular round, white 18A1 seeds each.

*The Flower*

Bud:
- *Color.*—White, 2A7, when calyx breaks.
- *Size.*—Just before calyx breaks, the bud is about 2½ inches long by 1¾ inches across.
- *Shape.*—Round base.
- *Peduncle.*—About 4 inches long, redder than stem.

Bloom:
- *Color.*—Pure white, 1A7, in late stages of bloom, may show red spots and blending of red at base.
- *Size.*—Fully opened flower reaches 4 to 5½ inches across.
- *Form.*—Five rings of petals.
- *Fragrance.*—Strongly scented.
- *Longevity.*—Lasts moderately well both on plant and as cut flower.
- *Frequency.*—Appear as single flowers or occasionally in clusters up to four in number.

Petals:
- *Size.*—Outer petals are about 2 inches long by 1½ inches wide.
- *Number.*—35 to 37 petals per bloom under normal conditions.
- *Shape.*—Spoon shaped.

*Reproductive Organs*

Pistils: Red orange, 2D12.
Stamens: Yellow, 9K1, brown tipped.

Having thus disclosed the invention, what is claimed is:

The new and distinct variety of climbing hybrid tea rose plant characterized particularly by its pure white blooms, vigorous, sturdy growth, strong scent and heavy canes.

No references cited.